United States Patent [19]

Suykerbuyk et al.

[11] Patent Number: 6,156,934

[45] Date of Patent: *Dec. 5, 2000

[54] DIPHOSPHINES

[75] Inventors: Jacoba Catherina Lucia Johanna Suykerbuyk; Eit Drent, both of CM Amsterdam, Netherlands; Paul Gerard Pringle, Bristol, United Kingdom

[73] Assignee: Shell Oil Company, Houston, Tex.

[ * ] Notice: This patent issued on a continued prosecution application filed under 37 CFR 1.53(d), and is subject to the twenty year patent term provisions of 35 U.S.C. 154(a)(2).

[21] Appl. No.: 08/987,555

[22] Filed: Dec. 9, 1997

[30] Foreign Application Priority Data

Mar. 26, 1997 [EP] European Pat. Off. .............. 97302079
Apr. 30, 1997 [EP] European Pat. Off. .............. 97302958

[51] Int. Cl.$^7$ ....................................................... C07F 9/50
[52] U.S. Cl. ................................................................ 568/12
[58] Field of Search ................................................ 568/12

[56] References Cited

U.S. PATENT DOCUMENTS

| | | |
|---|---|---|
| 3,026,327 | 3/1962 | Epstein . |
| 3,050,531 | 8/1962 | Epstein . |
| 4,230,641 | 10/1980 | Bartish ................................... 568/454 |
| 4,915,794 | 4/1990 | Slaugh et al. ............................. 203/29 |
| 4,946,560 | 8/1990 | Slaugh et al. ............................. 203/38 |
| 5,012,034 | 4/1991 | Weingaertner et al. ................ 585/806 |

FOREIGN PATENT DOCUMENTS 495 547 A2   7/1992   European Pat. Off. ........ C07C 51/14

OTHER PUBLICATIONS

"Precious Metal Complexes of Some Novel Functionalized Secondary and Tertiary Phosphines", by Ms. J. H. Downing, Nov. 1992, a thesis. pp. 1–200.

*Primary Examiner*—Jean F Vollano

[57] ABSTRACT

The invention relates to a diphosphine of the following formula $$R^1{>}P{-}R^2{-}PR^3R^4$$

wherein $R^2$ represents a covalent bridging group, $R^1$ represents a bivalent radical that together with the phosphorus atom to which it is attached is an optionally substituted 2-phospha-tricyclo[3.3.1.1{3,7}]decyl group or a derivative thereof in which one or more of the carbon atoms are replaced by heteroatoms ("6-PA" group), and wherein $R^3$ and $R^4$ independently represent univalent radicals of up to 20 atoms or jointly form a bivalent radical of up to 20 atoms; to carbonylation catalysts obtainable by combining: (i) a metal cation selected from the groups 8, 9 or 10 of the Periodic Table of Elements, and (ii) the new diphosphine; and furthermore to a process for carbonylating unsaturated compounds in the presence of the carbonylation catalyst.

9 Claims, No Drawings

DIPHOSPHINES

FIELD OF THE INVENTION

The invention relates to novel diphosphines, novel carbonylation catalysts and a process for the carbonylation of unsaturated compounds by reaction thereof with carbon monoxide and a coreactant in the presence of the novel carbonylation catalysts.

BACKGROUND OF THE INVENTION

Carbonylation reactions are known in the art. For instance, in EP-A-0,495,547 several examples are disclosed wherein olefins are converted into (thio)esters, acids, anhydrides, and amides, etc., depending on the nature of the coreactant. Other examples on the synthesis of aldehydes; ketones; carboxylic acids; esters; amides and other carboxylic acid derivatives; lactones; lactams and related N-heterocycles as well as background references can be found in "Carbonylation" by H M Colquhoun, D J Thompson and M V Twigg (Plenum press 1991). Typically, the rate of reaction is in the order of up to several hundreds moles product per mol catalyst (based on the metal) per hour. In case of internal unsaturation, the rate of reaction is several orders lower. In other words, either relatively large amounts of catalyst are required or prolonged reaction times are involved.

SUMMARY OF THE INVENTION

The present inventors set out to provide a more active carbonylation catalyst. Surprisingly, carbonylation catalysts with high activity have been found that are obtainable by combining:

(i) a metal cation selected from the groups 8, 9 or 10 of the Periodic Table of Elements, and (ii) a diphosphine of the following formula

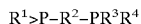

wherein $R^2$ represents a covalent bridging group, $R^1$ represents a bivalent radical that together with the phosphorus atom to which it is attached is an optionally substituted 6-phospha-tricyclo[3.3.1.1{3,7}]decyl group or a derivative thereof in which one or more of the carbon atoms are replaced by heteroatoms, and wherein $R^3$ and $R^4$ independently represent univalent radicals of up to 20 atoms or jointly form a bivalent radical of up to 20 atoms. In a further embodiment of the invention, there is included the diphosphines used in the preparation of these carbonylation catalysts.

SUMMARY OF THE INVENTION

Tricyclo[3.3.1.1{3,7}]decane is the systematic name for a compound more generally known as adamantane. Therefore, the optionally substituted 6-phospha-tricyclo[3.3.1.1{3,7}] decyl group will be referred to as "6-PA" group (as in 6-phosphadamantyl group) throughout the specification.

Preferably, the 6-PA group is substituted on one or more of the 1, 3, 5 or 7 positions with a monovalent radical $R^5$ of up to 20 atoms. Typical examples of $R^5$ include methyl, trifluoromethyl, ethoxy, phenyl, and 4-dodecylphenyl. More preferably, the 6-PA group is substituted on each of the 1, 3, 5 and 7 positions, suitably with identical radicals $R^5$.

The 6-PA group has preferably additional heteroatoms other than the 6-phosphorus atom in its skeleton. Suitable heteroatoms are oxygen and sulphur atoms. Suitably, these heteroatoms are found in the 2, 4 and 8 positions.

The most preferred bivalent radical is the 6-phospha-1,3,5,7-tetramethyl-2,4,8-trioxadamantyl group.

Each of the monovalent radicals $R^3$ and $R^4$ may independently be selected from (substituted) hydrocarbyl groups such as, for instance, methyl, phenyl, pyridyl, or o,o-di(t-butoxy)phenyl, and (substituted) heterohydrocarbyl groups such as, for instance, trimethylsilyl or alkoxy groups. Alternatively, $R^3$ and $R^4$ may together form a bivalent radical, such as 1,6-hexylene, 1,3 or 1,4-cyclooctylene, etc. Preferably, $R^3$ and $R^4$ together form a 6-PA group, most preferably a bivalent radical identical to $R^1$.

The preferred ligands to be used in the carbonylation catalysts of the present invention are 1,2-P,P'-di(6-phospha-1,3,5,7-tetramethyl-2,4,8-trioxa-adamantane)ethane (DPA2); 1,3-P,P'-di(6-phospha-1,3,5,7-tetramethyl-2,4,8-trioxa-adamantane)propane (DPA3); 1,2-P,P'-di-perfluoro (6-phospha-1,3,5,7-tetramethyl-2,4,8-trioxa-adamantane) ethane (FDPA2); and 1,3-P,P'-di-perfluoro(6-phospha-1,3,5,7-tetramethyl-2,4,8-trioxa-adamantane)propane (FDPA3); DPA3 being most preferred.

The ligand so defined can be prepared in a manner similar to the process for preparing the secondary phosphine 1,3,5,7-tetramethyl-2,4,8-trioxa-6-phosphaadamantane disclosed in chapter 3 of "PRECIOUS METAL COMPLEXES OF SOME NOVEL FUNCTIONALISED SECONDARY AND TERTIARY PHOSPHINES" by Ms. Joanne H Downing (theses submitted to the University of Bristol on November 1992). For instance, DPA3 is prepared by adding 2,4-pentanedione to 1,3-diphosphinopropane. Asymmetric ligands may be prepared using, for instance, a diphosphine having a tertiary phosphino group and a primary phosphino group. Alternatively, they may be prepared by coupling a secondary 6-phospha-tricyclo[3.3.1.1{3,7}]decane with another secondary monophosphine or by other processes known in the art. Substituted ligands can, for example, be made using substituted 2,4-pentanediones in the reaction with the phosphine.

According to the present IUPAC notation, group 8, 9 and 10 metal cations are cations of Fe, Ru, Os; Co, Rh, Ir and Ni, Pd, and Pt, respectively. These cations, as is illustrated in "Carbonylation", may each be used in the various carbonylation reactions.

Group 10 metal cations (referred to in the older literature as the platinum group metal cations) have been found to provide good results when used in the novel catalyst of the present invention.

Suitable sources for the metal cations may be found in "Carbonylation" and will form no problem to the person skilled in the art. Likewise, the preparation of the catalyst system (actually a precursor, the active species formed in-situ may be slightly different from that of the precursor here disclosed) follows the general recipe disclosed in the thesis by Ms J H Downing.

The catalyst systems may be used in the various carbonylation reactions described in EP-A-0,495,547 and in "Carbonylation". They are particularly excel in respect of the reaction rate when applied in the additive carbonylation of unsaturated compounds, in particular of ethylenically unsaturated compounds. The latter reaction, here shown for an alpha-olefin, proceeds according to the following reaction: $RCH=CH_2 + CO + HY \rightarrow RCH_2CH_2COY$; Y=H, OH, OR, $NR_2$, etc. The additive carbonylation of internal olefins is similar. However, due to its high isomerisation activity, the products typically resemble those of the reaction with the corresponding alpha-olefin.

In other words, the catalyst systems may be used in "hydroformylation reactions", "hydrocarboxylation reactions", "hydroesterification reactions", "hydroamidation reactions", etc.

It will be understood that in such carbonylation reactions coreactants, solvents, etc. may be used. In particular, various anions may be used as counter-ion to the metal cation. Examples thereof include anions that are the conjugated base of acids having a pKa (measured at 18° C. in water) of less than 6, preferably less than 4. The anions derived from these acids do not or only weakly co-ordinate with the metal cation, by which is meant that little or no covalent interaction occurs between the anion and the cation. Catalysts based on these anions exhibit a good activity.

Suitable anions include anions derived from Bronsted acids, such as from phosphoric acid and sulphuric acid, and in particular from sulphonic acids and (halogenated) carboxylic such as trifluoroacetic acid, 2,6-dichlorobenzoic acid, and 2,6-bis(trifluoromethyl)benzoic acid or trifluoroacetic acid, etc. Anions derived from sulphonic acids are particularly preferred, for example methanesulphonic acid, trifluoromethanesulphonic acid, tert-butanesulphonic acid, p-toluenesulphonic acid and 2,4,6-trimethylbenzenesulphonic acid.

Also, complex anions are suitable, such as the anions generated by a combination of a Lewis acid such as $BF_3$, $B(C_6F_5)_3$, $AlCl_3$, $SnF_2$, $Sn(CF_3SO_3)_2$, $SnCl_2$ or $GeCl_2$, with a protic acid, preferably having a pKa of less than 5, such as a sulphonic acid, e.g. $CF_3SO_3H$ or $CH_3SO_3H$ or a hydrohalogenic acid such as HF or HCl, or a combination of a Lewis acid with an alcohol. Examples of such complex anions are $BF_4^-$, $SnCl_3^-$, $[SnCl_2.CF_3SO_3]^-$ and $PF_6^-$.

The carbonylation reaction is conveniently carried out at moderate temperatures.

Accordingly, the process is suitably carried out at a temperature in the range of 30 to 200° C., preferred temperatures being in the range of 50 to 180° C. The reaction pressures may also vary widely. For instance, the reaction can be carried out with pressures in the range of 1 to 200 bar gauge, pressures in the range of 5 to 60 barg being preferred.

Carbon monoxide is preferably supplied in molar excess over the unsaturated compound and the coreactant "YH". In addition, the unsaturated compound and the coreactant are suitably supplied in a molar ratio within the range of 10:1 to 1:10, preferably within the range of 5:1 to 1:5, more preferably within the range of 2:1 to 1:2.

The quantity in which the catalyst system is used, is not critical and may vary within wide limits. Usually amounts in the range of $10^{-8}$ to $10^{-1}$, preferably in the range of $10^{31\ 7}$ to $10^{-2}$ mole atom of metal per mole of unsaturated compound are used.

For the preparation of the catalyst systems of the invention, the amount of ligand is generally applied in some excess of the amount of the Group 8 metal cation, expressed as moles of ligand per mole atom of the cation. Typically the amount of ligand is selected such that per mole atom of the cation 0.5 to 10 moles of ligand are present. However, for the preferred catalyst system the active species is believed to be based on an equimolar amount of bidentate ligand per mole cation. Thus, the molar amount of bidentate ligand per mole of cation is preferably in the range of 1 to 3, more preferably in the range of 1 to 2. In the presence of oxygen, slightly higher amounts may be beneficial. The amount of the anion source may range from 0.5 to 15, preferably from 1 to 8 moles per mole of cation.

In the process of the invention, the starting materials and the formed carbonylation products may act as reaction diluent. Hence, the use of a separate solvent is not necessary. Conveniently, however, the carbonylation reaction may be carried out in the additional presence of a solvent. As such, saturated hydrocarbons such as, e.g., paraffins and isoalkanes are recommended and furthermore ethers such as 2,5,8-trioxanonane (diglyme), diethylether and anisole; sulphones such as sulpholane, and aromatic hydrocarbons such as toluene.

The unsaturated compound may have one or more unsaturated bonds and is preferably an olefin having from 2 to 30 carbon atoms per molecule. The unsaturated bond(s) may be internal or terminal, the catalyst being particularly advantageous in the conversion of internal olefins. Particularly preferred are olefins having from 2 to 22 carbon atoms per molecule, such as ethene, propene, 1- or 6-butene, 1- or internal hexene, 1 or internal octene, diisobutylene, triisobutylene, tripropylene, internal decene, internal C14 olefins, and internal C15–C18 olefins.

In the unsaturated compound one or more hydrogen atoms may have been substituted by other atoms, such as halogen atoms or by groups of atoms, such as hydroxyl groups, cyano groups, such as methoxy or ethoxy groups, or amino groups such as dimethyl- and diethyl-amino groups.

Another preferred category of unsaturated compounds, consists of unsaturated esters of carboxylic acids and esters of unsaturated carboxylic acids. For example, the starting material may be a vinyl ester of a carboxylic acid such as acetic acid or propanoic acid, or it may be an alkyl ester of an unsaturated acid, such as the methyl or ethyl ester of acrylic acid or methacrylic acid.

A further preferred category of unsaturated compounds, consists of cycloalkadienes, which will ordinarily refuse carbonylation. For example, the starting material may be dicyclopentadiene or norbornadiene, to give diesters, diamides or diacids, etc., which may find use as monomer in polymerization reactions.

Suitable coreactants in the additive carbonylation process of the invention include compounds comprising a nucleophilic moiety and a mobile hydrogen atom.

Preferred nucleophilic compounds include: molecular hydrogen, water and alcohols, e.g., monohydric alcohols, such as methanol, ethanol, isopropanol and 1-butanol, and polyhydric alcohols, such as ethyleneglycol, 1,4-butanediol and glycerol; thiols; primary or secondary (poly-) amines or amides, such as diethylaamine, N,N-dimethyl ethylenediamine; aromatic alcohols and carboxylic acids, for example acetic acid, pivalic acid and propanoic acid. Molecular hydrogen, monohydric alcohols having from 1 to 6 carbon atoms per molecule and dihydric alcohols having from 2 to 6 carbon atoms per molecule are preferred.

1-Butanol, methanol and 1,4-butanediol are especially preferred. The use of these compounds as coreactants enables the production of valuable carbonylation products, such as methyl propanoate, butyl propanoate and 1,4-diacyloxy butanes. These compounds are of commercial interest and may be used as solvents and in flavouring compositions and perfumes.

Another preferred class of coreactants is composed of alkylphenols, wherein one or more alkyl groups of up to 30, typically 6 to 22 carbon atoms are attached to the phenol molecule. Additive carbonylation with these coreactants produces alkylphenyl esters that may find use as synthetic lubricants in industrial application, but in particular in automotive engines.

EXAMPLES

The invention will now be further described in the following examples, however, without restricting its scope. All experiments were carried out in a magnetically stirred 250 ml autoclave unless otherwise indicated. The abbreviations used in the Tables have the following meanings:

DPA3=1,3-P,P'-di(6-phospha-1,3,5,7-tetramethyl-2,4,8-trioxatricyclo[3.3.1.1{3.7}]decyl)propane MSA=methanesulphonic acid

Example 1 (Synthesis of DPA3)

4.63 Mmol diphosphinopropane was added to a solution of 27.8 mmol 2,4-pentanedione in 20 ml 5M HCl. After 1 hr stirring a white solid began to precipitate. The reaction mixture was stirred for a further 24 hrs, and then the volatile components were removed to leave a white, air-stable solid product. The product was washed with water (6×20 ml), dissolved in 20 ml dichloromethane and dried over magnesium sulphate, This solution was filtered and concentrated under vacuum to 1 ml. 10 ml pentane was added to precipitate the purified product, which was then recovered. (0.75 g, 34% yield). 1HNMR (400 MHz, in CD2C12), d 1.18 (6H, s), d 1.22 (18H, s), d 1.4–1.9 (m, 14H); 31P NMR (162 MHz): d −30.0, −30.8 ppm; mass spectrum showed m/e 472 (M+). These data confirm the nature of the product.

Example 2 (Carbonylation)

The autoclave was charged with 50 ml of methanol, 0.1 mmol of palladium(II) acetate, 0.15 mmol of DPA3, and 0.2 mmol of MSA. After being flushed, the autoclave was pressurised with carbon monoxide and ethene to a partial pressure of 30 bar and 20 bar respectively. Next, the reactor was sealed. The contents of the autoclave were heated to a temperature of 90° C. and maintained at that temperature for 0.25 hours. After cooling, a sample was taken from the contents of the autoclave and analysed by Gas Liquid Chromatography.

Ethene was fully converted with 100% selectivity into methyl propanoate at an average rate of 8000 mol per mole Pd per hour (mol/mol.hr).

Example 3

Example 2 was repeated, however using 10 ml water and 40 ml of diglyme as reactant/solvent and a process temperature of 110° C. The autoclave was cooled after 2 hours.

Ethene was fully converted with 100% selectivity into propanoic acid at an average rate of 1500 mol/mol.hr.

Example 4

Example 2 was repeated, however using 30 ml propene as olefin and a process temperature of 100° C.

Propene was fully converted with 78% selectivity into methyl butanoate and 22% selectivity into methyl 2-methylpropanoate at an average rate of 5000 mol/mol.hr.

Example 5

Example 2 was repeated, however using 20 ml 1-C14 as olefin. The autoclave was cooled after 3 hours.

The alpha-olefins were converted for 95% with 80% selectivity into linear methyl esters at an average rate of 250 mol/mol.hr.

Example 6

Example 2 was repeated, however using 20 ml i-C14 as olefin, at a process temperature of 115° C., and at a carbon monoxide pressure of 10 bar. The autoclave was cooled after 5 hours.

The internal olefins were converted for 93% with 78% selectivity into linear methyl esters at an average rate of 120 mol/mol.hr.

Comparative Example A

Example 6 was repeated, however 1,3-bis(di-tert-butylphosphino)propane as ligand, and at a carbon monoxide pressure of 10 and 30 bar, respectively. The autoclave was cooled after 10 hours.

The internal olefins were converted for only 10% with 75% selectivity into linear methyl esters at an average rate of 5 mol/mol.hr.

Example 7

Example 2 was repeated, however using 10 ml methyl 3-pentenoate as unsaturated compound, at a process temperature of 115° C. and at a carbon monoxide pressure of 15 bar. The autoclave was cooled after 6 hours.

Methyl 3-pentenoate was fully converted with 84% selectivity into linear dimethyl esters at an average rate of 100 mol/mol.hr.

What is claimed is:

1. A diphosphine of the following formula

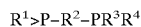

wherein $R^2$ represents a covalent bridging group, $R^1$ represents a bivalent radical that together with the phosphorus atom to which it is attached comprises an optionally substituted 6-phosphatricyclo[3.3.1.1{3,7}]decyl group or a derivative thereof in which one or more of the carbon atoms are replaced by oxygen or sulphur atoms, and wherein $R^3$ and $R^4$ independently represent univalent or bivalent, optionally substituted, hydrocarbyl groups or hetero hydrocarbyl groups of up to 20 atoms.

2. A diphosphine as claimed in claim 1, wherein the optionally substituted, 6-phospha-tricyclo[3.3.1.1{3,7}]decyl group is substituted on each of the 1, 3, 5 and 7 positions.

3. A diphosphine as claimed in claim 1, wherein the optionally substituted, 6-phospha-tricyclo decyl group comprises a 6-phospha-2,4,8-trioxa-1,3,5,7-tetramethyl-adamantane group.

4. A diphosphine as claimed in claim 1, wherein $R^3$ and $R^4$ together form an optionally substituted, 6-phospha-tricyclo[3.3.1.1{3,7}]decyl group when taken together with the phosphorus atom.

5. A diphosphine as claimed in claim 1, wherein $R^3$ and $R^4$ together form an optionally substituted, 6-phospha-tricyclo[3.3.1.1{3,7}]decyl group identical to $R^1$ when taken together with the phosphorus atom.

6. A diphosphine as claimed in claim 1, wherein the diphosphine is selected from the group consisting of 1,2-P,P'-di(6-phospha-1,3,5,7-tetramethyl-2,4,8-trioxa-adamantane)ethane; 1,3-P,P'-di(6-phospha-1,3,5,7-tetramethyl-2,4,8-trioxa-adamantane)propane; 1,2-P,P'-di-perfluoro(6-phospha-1,3,5,7-tetramethyl-2,4,8-trioxa-adamantane)ethane; and 1,3-P,P'-di-perfluoro(6-phospha-1,3,5,7-tetramethyl-2,4,8-trioxa-adamantane)propane.

7. The diphosphine 1,3-P,P'-di(6-phospha-2,4,8-trioxa-1,3,5,7-tetramethyl-adamantane)propane.

8. The diphosphine 1,3-P,P'-di(6-phospha-2,4,8-trioxa-1,3,5,7-tetramethyl-adamantane)ethane.

9. A diphosphine as claimed in claim 1, wherein said optionally substituted, 2-phospha-tricyclo[3.3.1.1{3,7}]decyl group is substituted at one or more of the 1,3,5 or 7 positions with a radical selected from the group consisting of methyl, trifluoromethyl, ethoxy, phenyl, and 4-dodecylphenyl.

* * * * *